(12) United States Patent
Ammerlaan

(10) Patent No.: US 8,772,578 B2
(45) Date of Patent: Jul. 8, 2014

(54) LETTUCE VARIETY 41-53 RZ

(75) Inventor: Aad Ammerlaan, Aramon (FR)

(73) Assignee: Ruk Zwaan Zaadteelt en Zaadhandel B.V., De Lier (NL)

( * ) Notice: Subject to any disclaimer, the term of this patent is extended or adjusted under 35 U.S.C. 154(b) by 1025 days.

(21) Appl. No.: 12/321,249

(22) Filed: Jan. 20, 2009

(65) Prior Publication Data

US 2009/0193535 A1    Jul. 30, 2009

Related U.S. Application Data

(60) Provisional application No. 61/023,616, filed on Jan. 25, 2008, provisional application No. 61/023,995, filed on Jan. 28, 2008.

(51) Int. Cl.
| | |
|---|---|
| A01H 1/00 | (2006.01) |
| A01H 4/00 | (2006.01) |
| A01H 5/00 | (2006.01) |
| A01H 5/10 | (2006.01) |
| C12N 15/82 | (2006.01) |

(52) U.S. Cl.
USPC .......... 800/305; 800/260; 800/278; 800/298; 435/410; 435/419

(58) Field of Classification Search
None
See application file for complete search history.

(56) References Cited

U.S. PATENT DOCUMENTS

| | | | | |
|---|---|---|---|---|
| 5,684,226 A | * | 11/1997 | Sarreal | 800/301 |
| 7,504,562 B2 | * | 3/2009 | Schut et al. | 800/305 |
| 7,652,196 B2 | * | 1/2010 | Ammerlaan | 800/305 |

OTHER PUBLICATIONS

Boggiatto Produce, Jun. 23, 2005.*
Lebeda et al, Chapter 9 Genetic Resources, Chromosome Engineering, and Crop Improvement, vol. 3, Vegetable Crops, 2007, Ram J. Singh editor, CRC press.*
Urban Farmer—website—2008.*
van der Arend and van Schijndel in Breeding for Resistance to insects and Mites, IOBC WPRS Bulletin 22(10), 35-43 (1999), abstract.*
Vigour Vegetable Seeds Website, Nov. 14, 2006.*
Eenink et al, Euphytica, 1982, vol. 31, pp. 291-300.*
IBEB press release "New race of *Bremia lactucae* BI:27 identified and nominated", May 2010; Plantum NL (Dutch association for breeding, tissue culture, production and trade . . .
Michelmore R. & Ochoa. O. "Breeding Crisphead Lettuce."In: California Lettuce Research Board, Annual Report 2005-2006, 2006, Salinas, California, pp. 55-68.
Schettini, T.M., Legg, E.J., Michelmore, R.W., 1991. Insensitivity to metalaxyl in California populations of *Bremia lactucae* and resistance of California lettuce cultivars . . .
Van Ettekoven, K. et al., "Identification and denomination of 'new' races of *Bremia lactucae*," In: Lebeda, A. and Kristkova, E (eds.), Eucarpia Leafy Vegetables, 1999 . . .
Van der Arend et al. "Identification and denomination of "new" races of *Bremia lactucae* in Europe by IBEB until 2002." In: Van Hintum, Th et al. (eds.), Eucarpia Leafy . . .

* cited by examiner

*Primary Examiner* — Eileen B O Hara
(74) *Attorney, Agent, or Firm* — Vedder Price P.C.; Thomas J. Kowalski; Deborah L. Lu

(57) ABSTRACT

The present invention relates to a *Lactuca sativa* L. var. *longifolia* Lam seed designated as 41-53 RZ, which has leaves with a solid main vein, narrow base leaves, and exhibits resistance against downy mildew (*Bremia lactucae* Regel), currant-lettuce aphid (*Nasonovia ribisnigri*) and lettuce mosaic virus (LMV). The present invention also relates to a *Lactuca sativa* L. var. *longifolia* Lam plant produced by growing the "41-53 RZ" seed. The invention further relates to methods for producing the lettuce cultivar, represented by lettuce variety 41-53 RZ.

21 Claims, 2 Drawing Sheets
(1 of 2 Drawing Sheet(s) Filed in Color)

LETTUCE VARIETY 41-53 RZ

INCORPORATION BY REFERENCE

This application claims priority to U.S. Provisional Application No. 61/023,616 filed Jan. 25, 2008 and U.S. Provisional Application No. 61/023,995 filed Jan. 28, 2008.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a new lettuce (*Lactuca sativa*) variety which may be suitable for mechanical harvest and resistant against *Nasonovia ribisnigri*.

BACKGROUND OF THE INVENTION

Romaine lettuce should provide a product at harvestable stage, which is accepted by processing industry and/or consumers. Therefore the harvestable product should not have tipburn, should have a short core, and it should have a dark green outer leaf color. Further it should be sufficiently headed, and as a result of this heading provide sufficient yellow-colored heartleaves.

Mature romaine lettuce is mainly harvested by hand. This harvesting process is labor-intensive, and relatively laborer-unfriendly. As it getting more and more costly to hire laborers that want to work outdoor in the field, close to the ground and under all kinds of adverse weather conditions, there is strong interest of the lettuce industry to mechanize this manual harvesting process. However, until now the lack of uniform quality among mature plants is big problem for mechanized harvest. Poor quality of basal leaves, internal breakdown of heartleaves due to tipburn, fringe burn of leaf margins, presence of aphids and fast bolting are the main quality problems. If one would like to mechanize the harvest process, these quality problems result in additional hand sorting, which is costly, and/or a very low net yield, if the plant parts with a high risk of quality problems are mechanically discarded. The latter approach is chosen by some producers that produce romaine hearts, i.e. the intact yellow-green heart of the romaine lettuce without the green outer leaves. For producers that produce romaine lettuce for processing, i.e. pre-washed and pre-cut leaves, this is not feasible because of four major constraints.

The first is the requirement for a mix of green and yellow leaves, which requires the preservation of the undamaged green outer leaves. The second constraint is the strongly reduced net yield, which is a result of the fact that an automated knife should cut through the leaf but not through the core. Especially fast bolting lettuce varieties are unacceptable for mechanized harvest of romaine lettuce for processing purposes because of their long core.

The third constraint is caused by the use of mechanically-driven horizontal knives that easily damage the hollow main veins of romaine leaves and cut halfway through the prostrate, round-shaped, lower outer leaves, which results in wide cut surfaces. Cutting damage on a leaf with a hollow main vein is often not restricted to the cut surface but bruising extends into the leaf along the main vein.

The fourth constraint is the presence of aphids. Besides their actual undesired presence in the product, they can also damage leaves and cause secondary rotting processes. Especially the currant-lettuce aphid *Nasonovia ribisnigri* is causing problems in lettuce, as it has the unique feature of multiplying deeply hidden in the heart of the lettuce plant. In the heart it cannot be reached by most insecticide treatments against aphids.

It is the object of the invention to provide a new type of romaine or cos lettuce, which is suitable for mechanical harvest with a simple horizontal knife and does not have problems with aphids. The harvested product is meant for processing purposes.

Citation or identification of any document in this application is not an admission that such document is available as prior art to the present invention.

SUMMARY OF THE INVENTION

The present invention fulfils this need by providing a new *Nasonovia*-resistant romaine, or cos, lettuce (*Lactuca sativa* L. var. *longifolia* Lam) plant, which exhibits a combination of leaves with a solid main vein, narrow base leaves, LMV-resistance and *Bremia*-resistance.

The present invention is further characterized by dark green outer leaves, a short core, absence of fringe burn, absence of tipburn and resistance to *Nasonovia ribisnigri*. The present invention provides seeds of the *Lactuca sativa* L. var. *longifolia* Lam plant designated as 41-53 RZ.

The present invention further provides pollen, ovules, and tissue cultures of regenerable cells from the plant produced by growing the seed of lettuce cultivar 41-53 RZ, in which the cells or protoplasts of the tissue that are cultured are produced from a tissue selected from leaves, pollen, embryos, cotyledon, hypocotyls, meristematic cells, roots, root tips, anthers, flowers, seeds or stems.

The present invention still further provides a lettuce plant regenerated from the above-described tissue cultures, in which the regenerated plant has all of the morphological and physiological characteristics of lettuce cultivar 41-53 RZ.

The present invention also provides a transgene of the seed of lettuce cultivar 41-53 RZ.

The present invention further provides a method for producing a hybrid lettuce seed comprising crossing a first parent lettuce plant with a second parent lettuce plant and harvesting the resultant hybrid lettuce seed, wherein the first parent lettuce plant or the second parent lettuce plant is the lettuce plant produced by growing the seed of lettuce cultivar 41-53 RZ.

The present invention still further provides a method for developing a lettuce cultivar having leaves with a solid main vein and narrow base leaves comprising crossing a mother lettuce plant cultivar with a father lettuce plant cultivar to produce a hybrid seed; growing the hybrid seed to produce a hybrid plant; selfing the hybrid seed to produce F2 progeny seed; and selecting the F2 plants for having leaves with a solid main vein and narrow base leaves.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

Deposits

The Deposits with the National Collections of Industrial, Marine and Food Bacteria (NCIMB) in Bucksburn, Aberdeen AB21 9YA, Scotland, UK, under deposit accession number 41536 were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings, in which.

DETAILED DESCRIPTION

An embodiment of the present invention provides *Lactuca sativa* L. var. *longifolia* Lam (romaine or cos lettuce) plant comprising leaves with a solid main vein and narrow base leaves, and resistance against the currant-lettuce aphid *Nasonovia ribisnigri*.

An embodiment of the present invention provides the *Lactuca sativa* L. var. *longifolia* Lam plant mentioned above with the following additional characteristics: resistance against downy mildew *Bremia lactucae*, and resistance against lettuce mosaic virus (LMV).

An embodiment of the present invention provides the *Lactuca sativa* L. var. *longifolia* Lam plant mentioned above with the following additional characteristics: dark green outer leaves, LMV-resistance, *Bremia*-resistance, short core, absence of fringe burn, and absence of tipburn.

A further embodiment of the present invention provides seeds of the *Lactuca sativa* L. var. *longifolia* Lam plant designated as 41-53 RZ, which have been deposited on Jan. 16, 2008, under the terms of the Budapest Treaty, with the National Collections of Industrial, Marine and Food Bacteria (NCIMB) in Bucksburn, Aberdeen AB21 9YA, Scotland, UK and have been assigned NCIMB Accession No. 41536. Deposited seed will be irrevocably and without restriction or condition released to the public during the effective term of any patent issued from this application As used herein, romaine is *Lactuca sativa* L. var. *longifolia* Lam; also known as cos. The plant develops in an upright open or upright compact growing habit with coarse textured leafs. The younger leaves are longer than they are wide, fifteen cupping together to form an elongated loose head. Leaf margins are often entire or undulated, rarely frilled. Outer leaves range in color from light green to dark green. Inner heartleaves are smaller and range from light yellow to light green in color.

Figure 1:
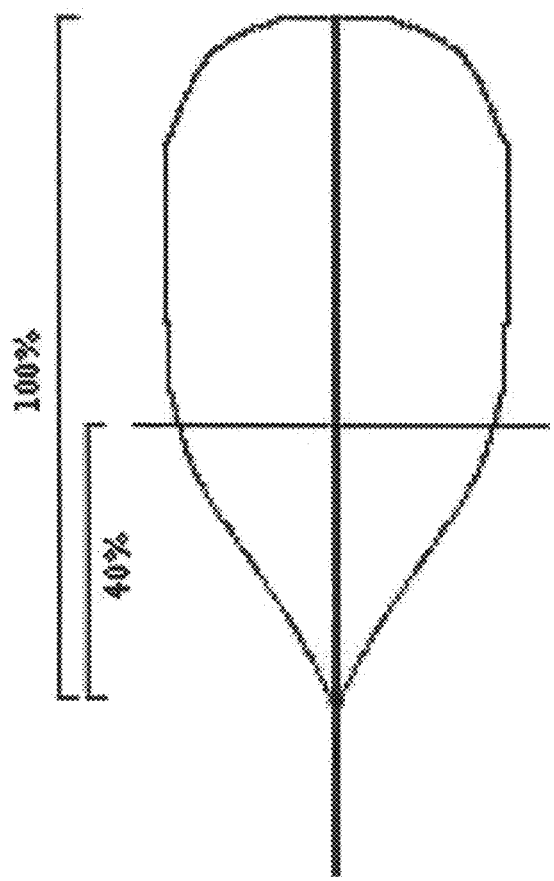
FIG. 1 shows a transverse section at 40% of leaf lamina length to observe solidness of main vein.

As used herein, a solid main vein is the main vein of a fully-grown tenth to fifteenth leaf, which is characterized by the fact that the vein is not hollow, which is observed by visual inspection of a transverse section of the leaf. The transverse section should be made at 40% of the total leaf length, starting from the leaf base (see FIG. 1). For comparison two standard varieties can be used: Maximus, with hollow veins, and Tiberius, with solid veins.

As used herein, a narrow base leaf is characterized by a length/width-ratio of 1.5 or higher. A mature romaine lettuce plant has got narrow base leaves if the average length/width-ratio of the fully-grown tenth to the fifteenth leaf is 1.5 or higher. For comparison two standard varieties can be used: Maximus with broad base leaves, and Chilim with narrow base leaves.

As used herein, resistance against *Bremia lactucae* Regal is defined as the ability of a plant to resist infection by various strains of *Bremia lactucae* (NL1, NL2, NL4, NL5, NL6, NL7, NL10, NL12, NL13, NL14, NL15, Bl:17, Bl:18, Bl:20, Bl:21, Bl:22, Bl:24, and Bl:25; Van Ettekoven K, Van der Arend A J M, 1999. In: Lebeda A, Kristkova E (eds.) Eucarpia leafy vegetables '99. Palacky University, Olomouc, Czech Republic, 1999: 171-175; Van der Arend et al., 2003. In: Van Hintum et al. (Eds.) Eucarpia Leafy Vegetables 2003. CGN, Wageningen, the Netherlands 2003: 151; Van der Arend et al., 2006. In: Pink et al. (Eds.) Eucarpia Leafy Vegetables 2006. Warwick HRI, Wellesbourne, UK, 2007 incorporated herein by reference) via a hypersensitivity response (Crute, I. R., Annual Rev. Phytopathol., 30:485-506, 1992; incorporated herein by reference).

Resistance is defined as the capacity of the plant to resist infection by each of the various strains of *Bremia lactucae* Regal in all stages between the seedling stage and the harvestable plant stage. Resistance typically is tested by two interchangeable methods, described by Bonnier, F. J. M. et al. (Euphytica, 61(3):203-211, 1992; incorporated herein by reference). One method involves inoculating 7-day old seedlings, and observing sporulation 10 to 14 days later. The other method involves inoculating leaf discs with a diameter of 18 mm obtained from a non-senescent, fully grown true leaf and observing sporulation 10 days later.

As used herein, resistance against *Nasonovia ribisnigri* (Mosley), or currant-lettuce aphid, is defined as the plant characteristic which results in a non-feeding response of the aphid on the leaves of the plant in all stages between 5 true-leaf stage and harvestable plant stage (U.S. Pat. No. 5,977, 443 to Jansen, J. P. A., "Aphid Resistance in Composites," p. 12, 1999; incorporated herein by reference).

Resistance is tested by spreading at least ten aphids on a plant in a plant stage between 5 true leaves and harvestable stage, and observing the density of the aphid population on the plant as well as the growth reduction after 14 days in a greenhouse, with temperature settings of 23 degrees Celsius in daytime and 21 degrees Celsius at night. Day length is kept at 18 hours by assimilation lights.

As used herein, resistance against lettuce mosaic virus (LMV) is defined as the ability of the plant to grow normally after LMV infection and to inhibit the virus transmission via seed. Resistance is tested by mechanical inoculation of young plants in a climate cell or a greenhouse, as described by Pink, D. A. C. et al. (Plant Pathology, 41(1):5-12, 1992), incorporated herein by reference. Inoculated resistant plants grow just as well as uninoculated plants and show no chlorosis or mosaic symptoms. The LMV isolate, which is used for testing, is Ls-1 (International Union for the Protection of New Varieties of Plants Varieties of Plants [UPOV], Guidelines for the conduct of tests for distinctness, uniformity and stability; lettuce (*Lactuca sativa* L.), 2002, p. 35; incorporated herein by reference).

As used herein, dark green outer leaves may be defined by the color of a fully-grown tenth to fifteenth leaf, which should be similar to or darker than 137B, 138A, 144A, or 146A on the RHS color chart (The Royal Horticultural Society, London, UK).

As used herein, a short core may be defined by measuring the length of the core of a harvested mature plant with outer leaves attached. The plant may be grown outdoor under long-day conditions: sowing 5-15 days before the longest day in a mild mid-latitude climate with a warm summer (Köppen-classification: Csb or Cfb; McKnight & Hess, 2000. Physical Geography: A Landscape Appreciation. Upper Saddle River, N.J.: Prentice Hall). A mature plant grown under these conditions may be defined as being headed and having a weight of 600-1000 g after harvest. The core of such a plant may be defined as 'short' if its length is less than or equal to 8 cm.

As used herein, absence of fringe burn may be established by growing plants in outdoor conditions in a winter production area for lettuce with an average daily temperature of the coldest month between 11 and 14 C, for example Cartagena, Spain or Yuma, USA. The growing cycle under these conditions may be at least 16 weeks from sowing a seed to harvesting a mature plant. Harvesting the mature plant may take place in the month after the coldest month. Absence of fringe burn may be defined by observing the leaf margin of the tenth until the fifteenth leaf. Absence of fringe burn may established, if for each of these leaves less than 2% of the perimeter of the leaf margin is necrotic.

As used herein, absence of tipburn may be established by growing plants in outdoor conditions in spring conditions in a winter production area for lettuce with an average daily temperature of the coldest month between 11 and 14 C, for example Cartagena, Spain or Yuma, USA. Harvesting the mature plant may take place in the third month after the coldest month. Absence of tipburn may be defined by observing the ten most recently developed heart leaves longer than 5 cm. Absence of tipburn may be established, if for each of these leaves less than 1% of the perimeter of the leaf margin is necrotic. The additional requirement for establishing absence of tipburn may be that the comparison variety Maximus, grown under the same conditions with the same sowing and harvest date, shows presence of tipburn, and a second comparison variety Optimus, grown under the same conditions with the same sowing and harvest date, shows absence of tipburn. Presence of tipburn may be established, if for at least one out of the ten most recently developed heart leaves longer than 5 cm, at least 1% of the perimeter of the leaf margin is necrotic.

In an embodiment of the present invention, there is provided a lettuce plant or parts thereof produced by growing the seed of lettuce cultivar 41-53 RZ.

In another embodiment, there is provided pollen, ovules, and tissue cultures of regenerable cells from the plant produced by growing the seed of lettuce cultivar 41-53 RZ, in which the cells or protoplasts of the tissue that are cultured are produced from a tissue selected from leaves, pollen, embryos, cotyledon, hypocotyls, meristematic cells, roots, root tips, anthers, flowers, seeds or stems.

In still another embodiment, there is provided a transgene of the seed of lettuce cultivar 41-53 RZ.

In a further embodiment, there is provided a lettuce plant regenerated from the above-described tissue cultures, in which the regenerated plant has all of the morphological and physiological characteristics of lettuce cultivar 41-53 RZ.

In still a further embodiment, a method is provided for producing a hybrid lettuce seed comprising crossing a first parent lettuce plant with a second parent lettuce plant and harvesting the resultant hybrid lettuce seed, wherein the first parent lettuce plant or the second parent lettuce plant is the lettuce plant produced by growing the seed of lettuce cultivar 41-53 RZ.

In still another embodiment, a method is provided for developing a lettuce cultivar having leaves with a solid main vein and narrow base leaves comprising crossing a mother lettuce plant cultivar with a father lettuce plant cultivar to produce a hybrid seed; growing the hybrid seed to produce a hybrid plant; selfing the hybrid seed to produce F2 progeny seed; and selecting the F2 plants for having leaves with a solid main vein and narrow base leaves.

In a preferred embodiment, the specific type of breeding method employed for developing a lettuce cultivar is pedigree selection, where both single plant selection and mass selection practices are employed. Pedigree selection, also known as the "Vilmorin system of selection," is described in Fehr, W., Principles of Cultivar Development, Volume I, Mac-Millan Publishing Co., which is hereby incorporated by reference.

When pedigree selection is applied, in general selection may be first practiced among F2 plants. In the next season, the most desirable F3 lines may be first identified, and then desirable F3 plants within each line may be selected. The following season and in all subsequent generations of inbreeding, the most desirable families may be identified first, then desirable lines within the selected families may be chosen, and finally desirable plants within selected lines may be harvested individually. A family refers to lines that were derived from plants selected from the same progeny from the preceding generation.

Using this pedigree method, two parents may be crossed using an emasculated female and a pollen donor (male) to produce F1 offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization.

Parental varieties are selected from commercial varieties that individually exhibit one or more desired phenotypes. Additionally, any breeding method involving selection of plants for the desired phenotype can be used in the method of the present invention.

The F1 may be self-pollinated to produce a segregating F2 generation. Individual plants may then be selected which represent the desired phenotype in each generation (F3, F4, F5, etc.) until the traits are homozygous or fixed within a breeding population.

The present invention is more particularly described in the following non-limiting example, which is intended to be illustrative only, as numerous modifications and variations therein will be apparent to those skilled in the art.

Example 1

Development and Characteristics of Lettuce Cultivar 41-53 RZ

The breeding history of the mother of 41-53 RZ started in Aramon, France in 1992 with a cross between a plant of the LMV-resistant romaine landrace 'Zaragozana' as mother and a plant from the *Bremia*-resistant romaine cultivar 'Remus' (Rijk Zwaan) as father with the aim to combine LMV- and *Bremia*-resistance. An F4-plant, '95A.5132', derived from this cross was selected in June 1995 in De Lier, the Netherlands and used as a father in a cross with a mother plant of the romaine cultivar 'Odra' (Nunhems) to combine the vigour of 'Odra' with the LMV- and *Bremia*-resistance of the father.

A *Bremia*- and LMV-resistant F5-plant, '98A.20110', derived from this cross was selected in October 1998 in Aramon, France and used as a father in a cross with a mother plant, which was a *Nasonovia*-resistant BC1.S2-plant, '98A.20150', derived from a backcross between the romaine variety 'Mikel' (Rijk Zwaan) as a recurrent parent and the *Nasonovia*-resistant iceberg cultivar 'Fortunas' (Rijk Zwaan) as a donor parent. An F3-plant, '01A.26137', was selected in June 2001 in Aramon, France for its combination of *Nasonovia*- and LMV-resistance. The *Bremia*-resistance was lost during the inbreeding process. This F3-plant was used as a mother in the final cross that led to 41-53 RZ.

The breeding history of the father of 41-53 RZ started in Aramon, France in 1995 with a cross between a plant from the grasse lettuce cultivar 'Bambi' (Rijk Zwaan) as mother and a plant from the *Bremia*-resistant indoor batavia breeding line '95A.30955' (Rijk Zwaan) as father with the aim to introduce resistance against *Bremia lactucae* (Bl-resistance) in the grasse type. An F3-plant, '97A.23750', derived from this cross was selected in July 1997 in Aramon, France and used as a father in a cross with a mother plant of the romaine cultivar 'Fransesca' (S&G) to introduce Bl-resistance in the romaine type.

An F3-plant, '99A.23056', derived from this cross was selected in April 1999 in Aramon, France for its leaves with a solid main vein, its short core, dark green color, absence of fringe burn and its Bl-resistance and used as a father in a cross with a mother plant of the romaine cultivar 'Chilim' (S&G). 'Chilim' was chosen for its narrow base leaves. An F3-plant, '01A.26065', derived from this cross, was selected in June 2001 in Aramon, France for being a dark green romaine type with leaves with a solid main vein, absence of tipburn, a short core, and narrow base leaves. This F3-plant was used as a father in the final cross that led to 41-53 RZ. Further inbreeding and selection of the offspring obtained by self-fertilization of this F3-plant resulted in the variety 'Actarus' (US patent application 'Cos for mechanical harvest').

The selected F3-plants '01A.26137' and '01A.26065' were crossed in the summer of 2001 and the F1 was directly sown to produce F2-seed in a greenhouse in Aramon. The F2-seed, designated '02A.51213', was sown in an early summer trial in Fijnaart, the Netherlands in 2003. In June 2003 an F2-plant was selected from the trial for being a dark green, *Nasonovia*-, *Bremia*-, and LMV-resistant romaine type with leaves with a solid main vein, absence of tipburn, and narrow base leaves. The F2-plant produced F3-seed, designated '04A.51051', which was sown in an early summer trial in Fijnaart, the Netherlands in 2004.

In June 2004 an F3-plant was selected from the trial for being a dark green, *Nasonovia*-, *Bremia*-, and LMV-resistant romaine type with leaves with a solid main vein, absence of tipburn, and narrow base leaves. The F3-plant produced F4-seed, designated '05A.50625', which was sown in a spring trial in Tarascon, France in 2005. In April 2005 an F4-plant was selected from the trial for being a dark green, *Nasonovia*-, *Bremia*-, and LMV-resistant romaine type with leaves with a solid main vein, absence of tipburn, and narrow base leaves. The F4-plant produced F5-seed, designated 06A.50602, which was uniform for type, field performance, disease-resistance, bolting, absence of tipburn and fringe burn, leaves with a solid main vein, and narrow base leaves (all based on several trials in 2006). The F5-seed was used to sow a multiplication in Hoek van Holland, the Netherlands in March 2006. The plants showed phenotypical uniformity during seed production and seed was harvested for further trialling in 2007 on confidential sites. The seed lot designated by the introduction number '41-53 RZ'.

In Table 1 that follows, the traits and characteristics of the *Lactuca sativa* L. var. *longifolia* Lam romaine lettuce plant having the designation 41-53 RZ, are given compared to the mentioned comparison varieties, referred to as "Tiberius", "Maximus", "Optimus", and "Chilim".

TABLE 1

| Character | "41-53 RZ" | "Tiberius" | "Maximus" | "Optimus" | "Chilim" |
|---|---|---|---|---|---|
| Type | romaine or cos | romaine or cos | romaine or cos | romaine or cos | romaine or cos |
| hollow/solid main vein | Solid | solid | hollow | hollow | hollow |
| broad/narrow base leaves | narrow | broad | broad | broad | narrow |
| blond/dark green color | Dark | dark | dark | blond | blond |
| core length | Short | long | short | short | long |
| tipburn | absent | present | present | absent | present |
| fringe burn | absent | absent | absent | present | present |

In the Tables that follow, the traits and characteristics of the *Lactuca sativa* L. var. *longifolia* Lam romaine lettuce plant referred to as "41-53 RZ" are given compared to the most similar variety, referred to as "Actarus" and a standard regional check variety, referred to as "Parris Island." Observations were made in a trial in Wageningen, the Netherlands in 2007. Sowing date was 27 March; transplanting date was 24 April.

In Table 2, the seed color, cotyledon shape and characteristics of the fourth leaf of "41-53 RZ" is compared with "Actarus" and "Parris Island." RHS=Royal Horticultural Society colour chart code.

TABLE 2

Figure 2:
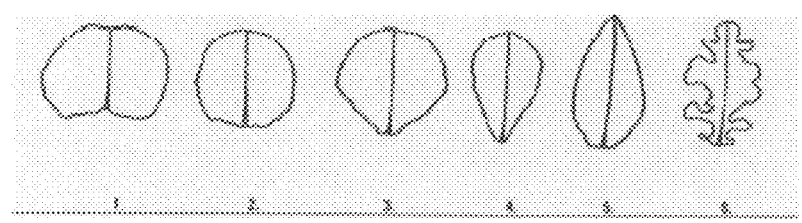
FIG. 2 shows possible shapes of cotyledon of fourth leaf.
Figure 3:
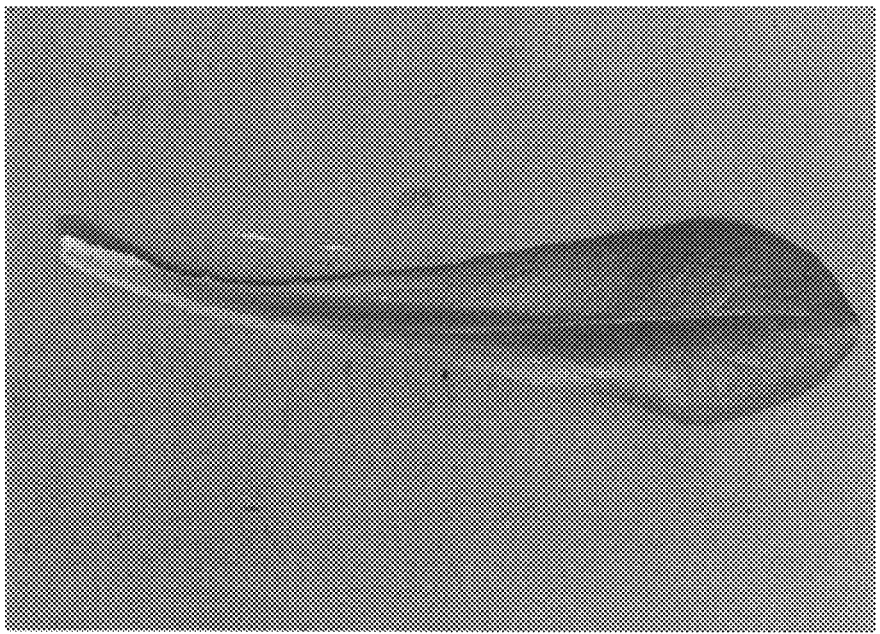
FIG. 3 shows a fourth leaf of 41-53 RZ.
Figure 4:
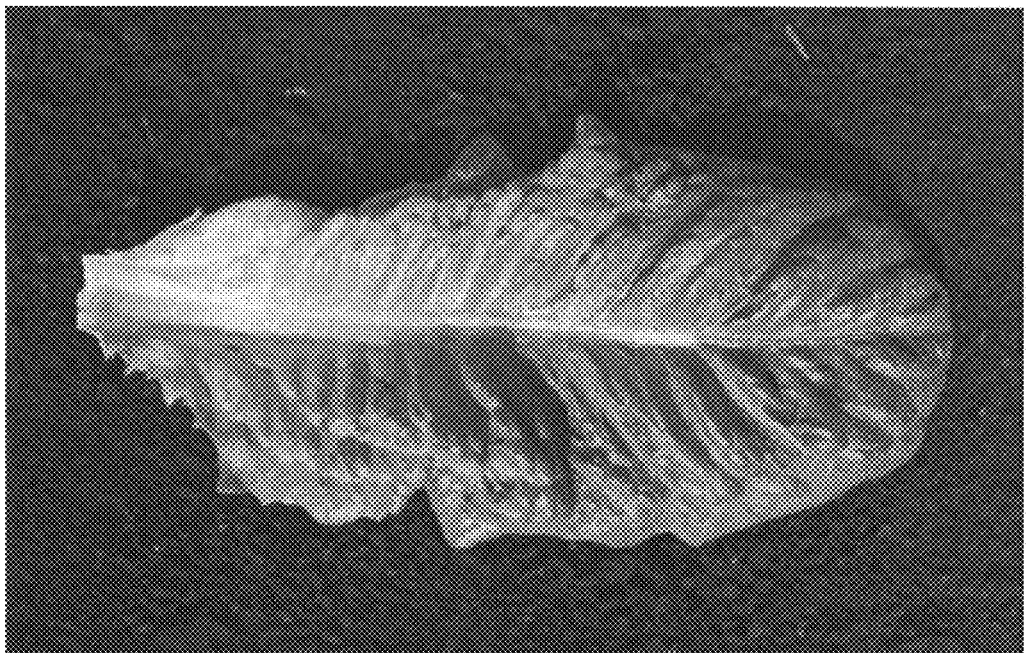
FIG. 4 shows a mature leaf of 41-53 RZ.

| Character | "41-53 RZ" | "Actarus" | "Parris Island" |
|---|---|---|---|
| Plant Type | Romaine or Cos | Romaine or Cos | Romaine or Cos |
| Seed Color | Black (Silver Gray) | White (Silver Gray) | White (Silver Gray) |
| Cotyledon Shape | Broad | broad | Intermediate |
| Cotyledon Shape of Fourth Leaf | No. 4 on FIG. 2 | No. 4 on FIG. 2 | No. 4 on FIG. 2 |
| Cotyledon Rolling of Fourth Leaf Stage | Absent | Absent | Absent |
| Cotyledon Cupping of Fourth Leaf Stage | Uncupped | Uncupped | Uncupped |
| Fourth Leaf Apical Margin | Entire | Entire | Entire |
| Fourth Leaf Basal Margin | Entire | Finely dentate (slightly) | Finely Dentate |
| Undulation | Flat | Flat | Flat |

In Table 3, the mature leaf and head characteristics of "41-53 RZ" is compared with "Actarus" and "Parris Island."

TABLE 3

| Character | "41-53 RZ" | "Actarus" | "Parris Island" |
|---|---|---|---|
| Maturity (Earliness of Harvest-Mature Head Formation (Spring season) | 76 days | 76 days | 71 days |
| Green Color | RHS 137B | RHS 137B | RHS 137A |
| Anthocyanin Distribution | Absent | Absent | Absent |
| Margin Incision Depth | Absent/Shallow | Absent/Shallow | Absent/Shallow |
| Margin Indentation | Shallowly Dentate | Shallowly Dentate | Shallowly Dentate |
| Undulations of the Apical Margin | Absent/Slight | Absent/Slight | Absent/Slight |
| Leaf Size | Large to Medium | Large to Medium | Large |
| Leaf Glossiness | Moderate | Moderate | Moderate to Dull |
| Leaf Blistering | Moderate | Moderate | Moderate |
| Leaf Thickness | Intermediate | Intermediate | Intermediate to Thick |
| Trichomes | Absent (Smooth) | Absent (Smooth) | Absent (smooth) |
| Spread of Frame Leaves | 41 cm | 39 cm | 40 cm |
| Head Diameter | 14 cm | 14 cm | 14 cm |
| Head Shape | Elongate | Elongate | Elongate |
| Head Size | Medium | Medium | Large |
| Head Weight | 690 g | 675 g | 644 g |
| Head Firmness | Moderate | Moderate | Firm |
| Butt Shape | Rounded | Rounded | Rounded |
| Midrib | Prominently Raised | Prominently Raised | Prominently Raised |

In Table 4, the characteristics of the core and the bolter plant of "41-53 RZ" is compared with "Actarus" and "Parris Island."

TABLE 4

| Character | "41-53 RZ" | "Actarus" | "Parris Island" |
|---|---|---|---|
| Core Diameter at Base of Head | 44 mm | 40 mm | 46 mm |
| Ratio of Head Diameter/Core Diameter | 3.3 | 3.5 | 3.0 |
| Core Height from Base of Head to Apex | 74 mm | 69 mm | 84 mm |
| Number of Days from first water date to seed stalk emergence | 91 | 91 | 86 |
| Bolting Class | Very Slow | Very Slow | Slow |
| Height of Mature Seed Stalk | 82 cm | 70 cm | 93 cm |
| Spread of Bolter Plant | 25 cm | 35 cm | 25 cm |
| Bolter Leaves | Straight | Straight | Slightly Curved |
| Margin | Slightly Dentate | Dentate | Slightly Dentate |
| Color | RHS 137A | RHS 137A | RHS 137B |
| Terminal Inflorescence | Present | Present | Present |
| Lateral Shoots | Present | Present | Present |
| Basal Side Shoots | Present | Present | Present |

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications and variations of the method and apparatuses described herein will be obvious to those skilled in the art, and are intended to be encompassed by the following claims.

What is claimed is:

1. A lettuce plant designated 41-53 RZ, representative seed of which having been deposited under NCIMB Accession No. 41536, wherein said plant is a romaine lettuce (*Lactuca saliva* L. var. *longifolia* Lam) plant, and has leaves with a solid main vein, narrow base leaves and resistance to downy mildew (*Bremia lactucae* Regal), currant-lettuce aphid (*Nasonovia ribisnigri*) and lettuce mosaic virus (LMV).

2. A seed of the plant of claim 1.

3. A part of the plant of claim 1 that is suitable for sexual reproduction.

4. The part as described in claim 3, selected from the group consisting of microspores, pollen, ovaries, ovules, embryo sacs, and egg cells.

5. A part of the plant of claim 1 that is suitable for vegetative reproduction.

6. The part as described in claim 5 selected from the group consisting of cuttings, roots, stems, cells, and protoplasts.

7. A tissue culture of a lettuce plant of claim 1.

8. The tissue culture as described in claim 7, which is derived from the group consisting of leaves, pollen, embryos, cotyledon, hypocotyls, meristematic cells, roots, root tips, anthers, flowers, seeds and stems.

9. A plant that has all of the morphological and physiological characteristics of lettuce cultivar 41-53 RZ, representative seed of which having been deposited under NCIMB Accession No. 41536 and is grown from seeds as described in claim 2.

10. A plant that has all of the morphological and physiological characteristics of lettuce cultivar 41-53 RZ, representative seed of which having been deposited under NCIMB Accession No. 41536 and is regenerated from parts as described in claim 3.

11. A plant that has all of the morphological and physiological characteristics of lettuce cultivar 41-53 RZ, representative seed of which having been deposited under NCIMB Accession No. 41536 and is regenerated from a tissue culture as described in claim 7.

12. A F1 progeny of a lettuce plant of claim 1.

13. A F1 progeny of a lettuce plant of claim 9.

14. A F1 progeny of a lettuce plant of claim 10.

15. A F1 progeny of a lettuce plant of claim 11.

16. A F1 progeny of a lettuce plant of claim 1, wherein said plant is a romaine lettuce (*Lactuca saliva* L. var. *longifolia* Lam) plant, and has leaves with a solid main vein, narrow base leaves and resistance to downy mildew (*Bremia lactucae* Regal), currant-lettuce aphid (*Nasonovia ribisnigri*) and lettuce mosaic virus (LMV) as found in lettuce cultivar 41-53 RZ, representative seed of which having been deposited under NCIMB Accession No. 41536, and is modified in one or more other characteristics.

17. The progeny as described in claim 16, wherein the modification is effected by mutagenesis.

18. The progeny as described in claim 16, wherein the modification is effected by transformation with a transgene.

19. A method of producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of claim 1.

20. A F1 progeny of a lettuce plant of claim 1, wherein said progeny is produced by sexual reproduction of said lettuce plant, and wherein the progeny has all of the morphological and physiological characteristics of lettuce cultivar 41-53 RZ, representative seed of which having been deposited under NCIMB Accession No. 41536.

21. A progeny of a lettuce plant of claim 1, wherein said progeny is produced by vegetative reproduction of said lettuce plant or a progeny plant thereof, and wherein the progeny has all of the morphological and physiological characteristics of lettuce cultivar 41-53 RZ, representative seed of which having been deposited under NCIMB Accession No. 41536.

* * * * *